(12) United States Patent
Nguyen et al.

(10) Patent No.: US 12,318,530 B2
(45) Date of Patent: Jun. 3, 2025

(54) SYSTEMS AND METHODS FOR PERFORMING EXTRACORPOREAL PHOTOPHERESIS

(71) Applicant: Fenwal, Inc., Lake Zurich, IL (US)

(72) Inventors: Lan T. Nguyen, Vernon Hills, IL (US); Katherine N. Radwanski, Highland Park, IL (US); Greg Coultas, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 465 days.

(21) Appl. No.: 17/716,579

(22) Filed: Apr. 8, 2022

(65) Prior Publication Data

US 2022/0347368 A1 Nov. 3, 2022

Related U.S. Application Data

(60) Provisional application No. 63/174,173, filed on Apr. 13, 2021.

(51) Int. Cl.
*A61M 1/36* (2006.01)
*A61M 1/34* (2006.01)

(52) U.S. Cl.
CPC ........ *A61M 1/3681* (2013.01); *A61M 1/3401* (2022.05); *A61M 1/3403* (2014.02); *A61M 1/3406* (2014.02); *A61M 1/3496* (2013.01); *A61M 2202/0415* (2013.01)

(58) Field of Classification Search
CPC .............. A61M 1/3401; A61M 1/3403; A61M 1/3406; A61M 1/3472; A61M 1/3496; A61M 1/3681; A61M 1/3683; A61M 1/3686; A61M 1/3693; A61M 2202/0415

USPC ........................................ 604/4.01
See application file for complete search history.

(56) References Cited

U.S. PATENT DOCUMENTS

| | | | |
|---|---|---|---|
| 5,360,542 A | 11/1994 | Williamson, IV et al. | |
| 6,027,657 A | 2/2000 | Min et al. | |
| 7,433,030 B2 | 10/2008 | Waldo et al. | |
| 2015/0196706 A1* | 7/2015 | Radwanski | A61M 1/3696 422/44 |
| 2019/0099541 A1 | 4/2019 | Ali | |
| 2019/0269844 A1* | 9/2019 | Ali | A61M 1/3693 |

FOREIGN PATENT DOCUMENTS

| | | | |
|---|---|---|---|
| EP | 3501562 A1 | 6/2019 | |
| WO | WO-9622117 A2 * | 7/1996 | A61M 1/1692 |

OTHER PUBLICATIONS

The Extended European Search Report for European Application No. 22167614.1 mailed on Jan. 20, 2023.
The Extended European Search Report for European Application No. 24210817.3 mailed on Jan. 29, 2025.

\* cited by examiner

*Primary Examiner* — Andrew J Mensh
(74) *Attorney, Agent, or Firm* — Cook Alex Ltd.

(57) ABSTRACT

Systems and methods are disclosed for performing online extracorporeal photopheresis in which the needs of a particular patient as to the fluid balance to be achieved and the time allotted to perform the procedure can be prioritized. Whole blood is removed from a patient and introduced through a processing set into a separation chamber to separate the desired cell population from the blood. The separated cell population is processed through the set which is associated with a treatment chamber where the cells are treated. Once treated, the cells are returned to the patient.

16 Claims, 9 Drawing Sheets

SYSTEMS AND METHODS FOR PERFORMING EXTRACORPOREAL PHOTOPHERESIS

CROSS-REFERENCE TO RELATED APPLICATION

This patent application claims the benefit of U.S. Provisional Patent Application Ser. No. 63/174,173, filed Apr. 13, 2021, the disclosure of which is incorporated herein by reference in its entirety.

FIELD OF THE DISCLOSURE

The present disclosure relates to systems and methods for performing extracorporeal photopheresis ("ECP"). More particularly, the present disclosure is directed to systems and methods for performing ECP in which procedure and/or photoactivation duration is estimated based on the predicted contents of the treatment container, patient-specific requirements are considered, and, if required, the contents of the treatment container are varied so that the procedure meets the patient-specific requirements.

BACKGROUND

Whole blood is made up of various cellular and non-cellular components such as red cells, white cells and platelets suspended in its liquid component, plasma. Whole blood can be separated into its constituent components (cellular, liquid or other), and the separated component can be administered to a patient in need of that particular component.

The administration of blood and/or blood components is common in the treatment of patients suffering from disease. Rather than infuse whole blood, it is more typical that individual components be administered to the patient(s) as their needs require. For example, administration (infusion) of platelets is often prescribed for cancer patients whose ability to make platelets has been compromised by chemotherapy. Infusion of white blood cells (i.e., mononuclear cells), after the cells have undergone some additional processing or treatment, may also be prescribed for therapeutic reasons including treatment of diseases that specifically involve the white blood cells. Thus, it is often desirable to separate and collect the desired blood component from whole blood and then treat the patient with the specific blood component. The remaining components may be returned to the donor or retained for other uses.

Extracorporeal photopheresis (also sometimes referred to as extracorporeal photochemotherapy) is a process in which whole blood is withdrawn from a patient and separated to produce a volume of target cells that is treated and then returned to the patient. In one example, known as Extracorporeal Photopheresis (ECP), whole blood from a patient is separated to produce a volume of concentrated mononuclear cells (MNCs). The concentrated MNCs are collected in a treatment container to which a photoactive drug, 8-methoxypsoralen (8-MOP) is added. The container is then exposed to UV-A light to cause photoactivation of the 8-MOP, leading to crosslinked DNA in the MNCs that blocks the ability of the treated MNCs to proliferate. The treated MNCs are then reinfused into the patient.

In addition to the concentrated MNCs, the treatment container will also contain varying amounts of granulocytes, platelets, red blood cells, plasma, anticoagulant, and saline that are separated from the whole blood along with the MNCs. However, it is important to keep the concentration of these other components sufficiently low so that the transmission of UVA light to the target cells is not inhibited, so that the photoactivation time would need to be extended to ensure that an adequate dose of UV-A light is transmitted to the target cells. This is particularly true with respect to the concentration of red blood cells and with respect to plasma of low clarity due to the extent to which they absorb UV-A light.

To reduce the concentration of UV-A absorbing substances, the concentrated MNCs are commonly diluted with, e.g., saline to provide for a shortened photoactivation duration that still provides for effective treatment of the target cells. This is particularly important in the context of online ECP systems that keep the patient connected during the photoactivation process, as shorter treatment times are desirable for patient comfort. Diluting the concentrated MNCs also ensures that the MNCs are suspended in a sufficient volume of fluid to allow for proper pumping, mixing and/or agitation during the photoactivation period.

Dilution of the target cells will also result in an increased volume of the treated MNCs that are reinfused into the patient, which raises potential concerns about the effect of the reinfusion on the patient's fluid balance. This can be a particular issue in smaller/lower weight patients or children that have a relatively smaller total body fluid volume and for patients whose tolerance of discomfort may be less than that of a typical adult. In addition to issues regarding fluid balance, a patient may also be subject to constraints that limit the amount of time that that the patient may have to spend in an ECP procedure.

By way of the present disclosure, a method and system for performing ECP is provided in which the needs of a particular patient as to the fluid balance to be achieved and the time allotted to perform the procedure can be prioritized.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In a first aspect, a method for photoactivating a suspension of target cells separated from whole blood is provided comprising: establishing patient and procedure parameters, including a target % of plasma in the suspension of target cells and a target photoactivation time; estimating a fluid balance limit based on patient and procedure parameters; estimating a fluid balance level based on patient and procedure parameters; determining whether the estimated fluid balance level exceeds the estimated fluid balance limit; if the fluid balance limit is exceeded, i) increasing the target % of plasma in suspension of target cells and recalculating the estimated fluid balance until the recalculated fluid balance is within limit and extending the target photoactivation time proportional to target % plasma in suspension of target cells and/or ii) decreasing volume of WB to be processed and recalculating the fluid balance until the recalculated fluid balance is within limit; collecting a suspension of target cells that achieves a fluid balance within the estimated fluid balance limit; and subjecting the suspension of target cells to phototreatment for the target photoactivation time.

In a second aspect, a method for photoactivating a suspension of target cells separated from a volume of whole blood is provided comprising: establishing patient and procedure parameters, including an estimated target procedure time that includes an estimated photoactivation time, based on a target % of plasma in the suspension of target cells; determining a patient-specific procedure time limit; determining whether the estimated target procedure time exceeds the patient-specific procedure time limit; if the patient-specific procedure time limit is exceeded, i) decreasing the target % of plasma in the suspension of target cells and recalculating the estimated target procedure time until the recalculated target procedure time is within the donor-specific procedure time limit and/or ii) decreasing the volume of whole blood to be processed and recalculating the estimated target procedure time until the recalculated estimated target procedure time is within the patient-specific procedure time limit; collecting a suspension of target cells that achieves an estimated procedure time within the donor-specific procedure time limit; and subjecting the suspension of target cells to phototreatment for the estimated photoactivation time.

In a third aspect, a method for photoactivating a suspension of target cells separated from a volume of whole blood is provided comprising: establishing patient and procedure parameters, including an estimated photoactivation time for the suspension of target cells to be treated based on a default value for plasma clarity and a target % of plasma in suspension of target cells; separating whole blood into a first component comprising plasma and a second component; measuring a clarity for the plasma comprising the first component; comparing the measured plasma clarity to the default value for plasma clarity; if the measured plasma clarity differs from the default value for plasma clarity, estimating a new photoactivation time based on the measured value for plasma clarity and/or adjusting the target % of plasma in suspension of target cells to be treated to achieve the estimated photoactivation time; Collecting the suspension of target cells; and subjecting the suspension of target cells to phototreatment for the target photoactivation time.

In a fourth aspect, a method for photoactivating a suspension of target cells separated from a volume of whole blood is provided comprising: establishing patient and procedure parameters, including an estimated target procedure time that includes a target photoactivation time for the suspension of target cells to be treated based on a predicted hematocrit of the suspension of target cells and a target % of plasma in suspension of target cells to be treated; determining a patient-specific procedure time limit; determining whether the estimated target procedure time exceeds the patient-specific procedure time limit; if the patient-specific procedure time limit is exceeded, i) decreasing the hematocrit of the suspension of target cells and/or decreasing the % of plasma in the suspension of target cells, and recalculating the estimated target procedure time until the recalculated estimated target procedure time is within the patient-specific procedure time limit; collecting a suspension of target cells; and subjecting the suspension of target cells to phototreatment for the target photoactivation time.

DESCRIPTION OF THE ILLUSTRATED EMBODIMENTS

The subject matter of the present disclosure relates generally to systems and methods for performing online extracorporeal photopheresis (ECP) treatment of mononuclear cells. To provide a context for the various aspects described herein, a description follows of a multifunctional automated apheresis device, a disposable fluid circuit, and an independent irradiation device housed separately from the apheresis device.

Figure 1:
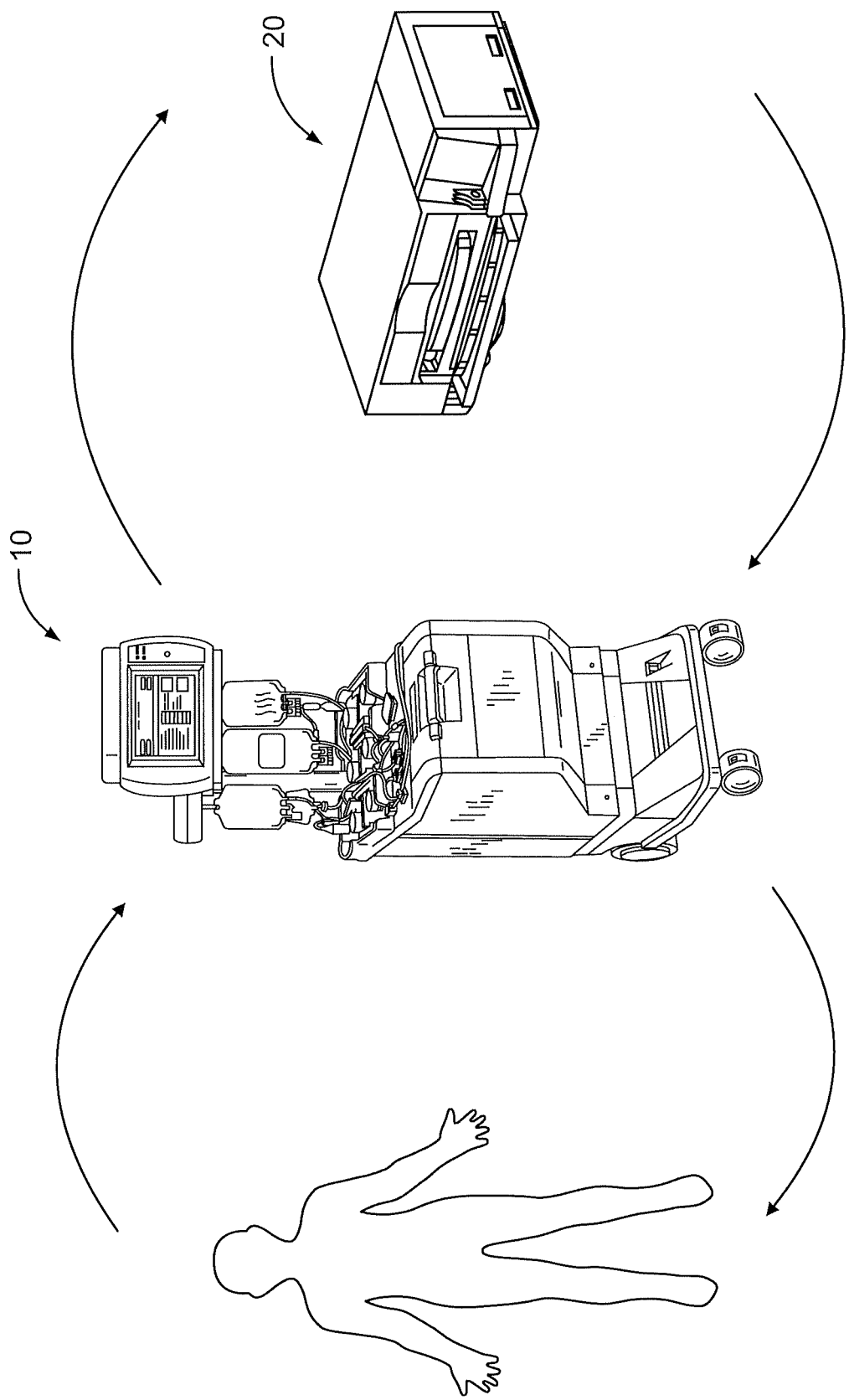
FIG. 1 is a diagram generally showing the mechanical components for performing a photopheresis treatment as described herein.

FIG. 1 shows, in general, the mechanical components that make up the system and that are used in the methods described herein. In accordance with the present disclosure, the system includes a separation component 10 and a treatment (i.e., irradiation) component 20. As shown, irradiation component 20 is independent and housed separately from separation component 10. However, the separation component and the irradiation component may be integrated into a single device without departing from the subject matter of the present disclosure.

Figure 4:
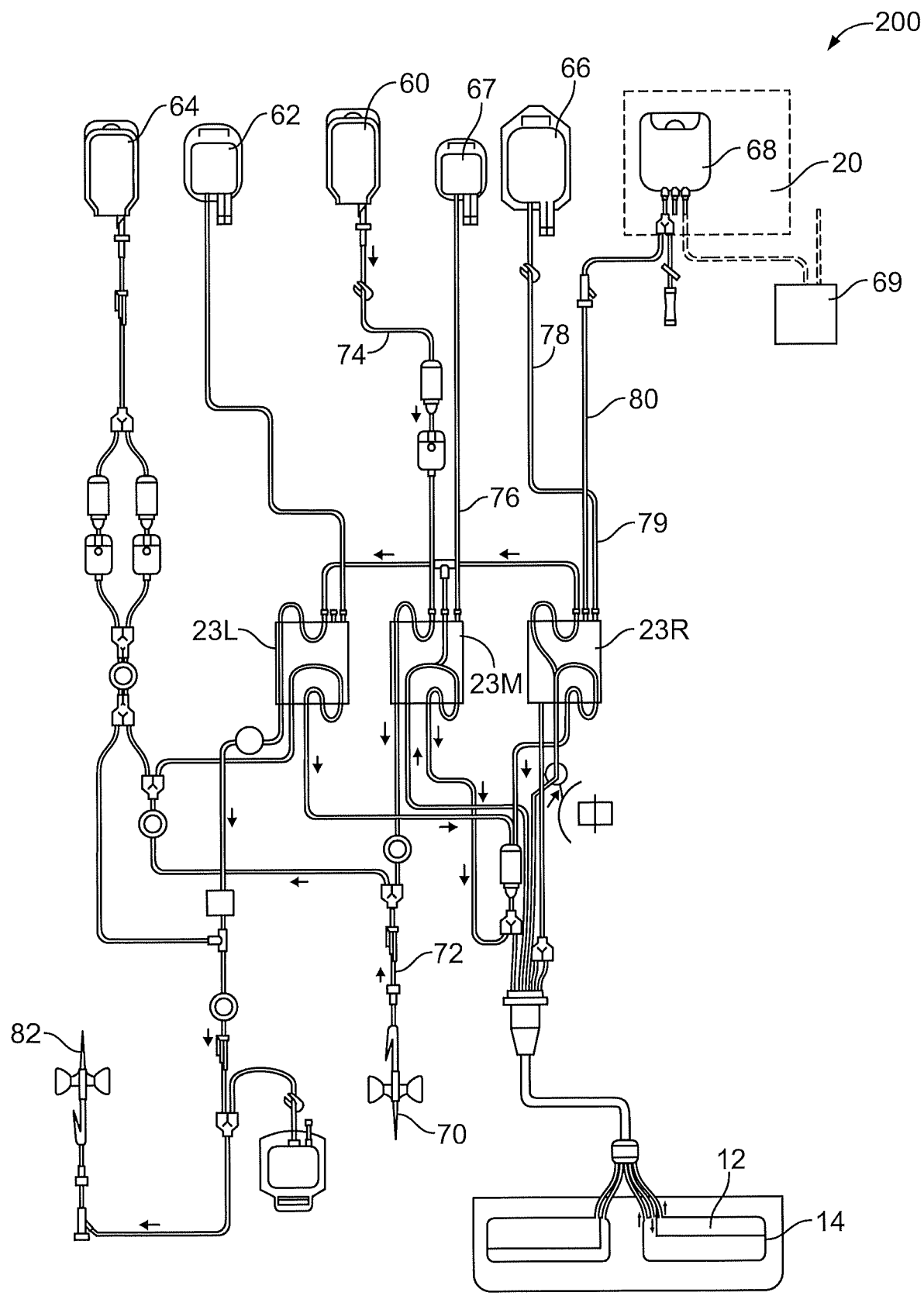
FIG. 4 is a diagram of the fluid circuit useful in the collection, treatment and reinfusion of mononuclear cells as described herein.

Although separately housed and independent devices, it is preferable that separation device 10 and irradiation device 20 are located adjacent to each other. In one example, separation device 10 and irradiation 20 may be located in the same room but physically spaced several feet or yards from each other. Irradiation device 20 may be on a table top located near or adjacent to separation component 10 allowing an operator or clinician to have access to both devices during a particular treatment procedure. In accordance with the systems and methods described herein a patient is connected to a blood processing set, i.e., fluid circuit 200. As generally illustrated in FIGS. 1 and 4, fluid circuit 200 provides a sterile closed pathway between separation component 10 and irradiation component 20. The system described herein also optionally includes a washing component which, preferably, is housed within the separation component. Preferably, the separation component 10 and washing component are one and the same, as will be described in greater detail below.

With reference to FIG. 1, whole blood is withdrawn from the patient and introduced into the separation component 10 where the whole blood is separated to provide a target cell population. In a preferred embodiment in accordance with the present disclosure, the target cell population may be mononuclear cells. Other components separated from the whole blood, such as red blood cells and platelets may be returned to the patient or collected in pre-attached containers of the blood processing set.

The separated target cell population, e.g., mononuclear cells, is then treated and irradiated in treatment component 20. As discussed above, treatment of mononuclear cells involves the photoactivation of a photoactive agent that has been combined with the mononuclear cells.

Once treated, the mononuclear cells may optionally be provided to a washing component, which, as shown in FIG. 1, is housed within separation component 10 and, preferably, is one and the same. The treated mononuclear cells are separated from the supernatant and the concentrated cells may be returned to the patient. The supernatant liquid will typically include excess and unbound photoactivation agent.

Optionally, the concentrated cells may further be combined with a suitable wash solution within separation/washing component 10. If washing of the treated mononuclear cells is performed, the suspension of mononuclear cells in a wash solution is then subjected to a centrifugal field (or other environment which can effect separation of the fluid components), whereby the mononuclear cells are concentrated and separated from the supernatant. The supernatant liquid may include any remaining unbound photoactivation agent. Supernatant may then be diverted to an appropriate waste container, while the treated mononuclear cells are returned to the patient, as generally shown in FIG. 1.

Apparatus useful in the collection (and washing) of mononuclear cells include the Amicus® Separator made and sold by Fenwal, Inc., of Lake Zurich, Illinois Mononuclear cell collections using a device such as the Amicus® are described in greater detail in U.S. Pat. No. 6,027,657, the contents of which is incorporated by reference herein in its entirety.

Figure 2:
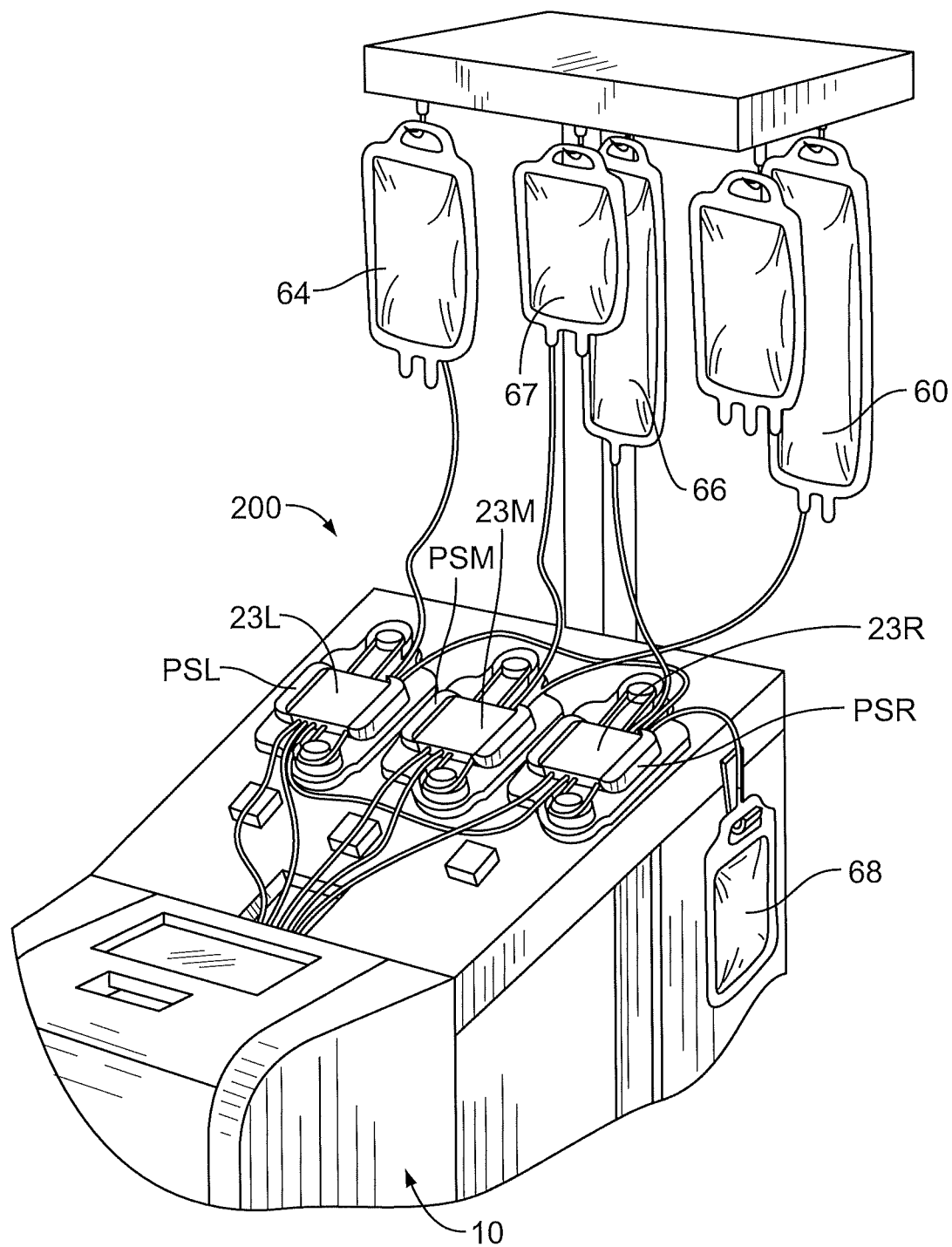
FIG. 2 is a partial perspective view of a multifunctional apheresis separator useful in the methods and systems described herein.
Figure 3:
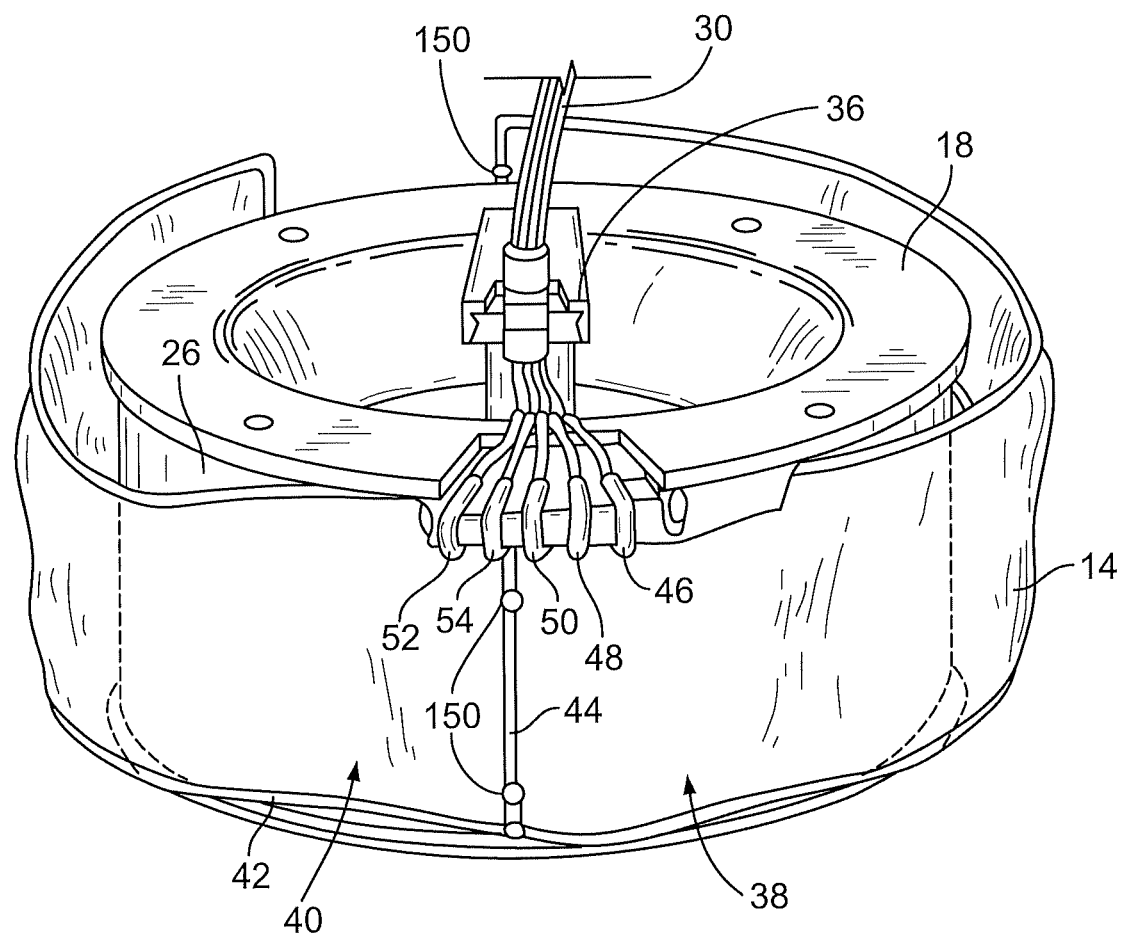
FIG. 3 is a perspective view of a processing container (separation chamber) of the processing set used with the separator of FIG. 2.

FIGS. 2-4 show a representative blood centrifuge 10 with fluid circuit 200 mounted thereon (FIG. 2), the fluid circuit (FIG. 4) having a blood processing container 14 (see FIG. 3) defining a separation chamber suitable for harvesting mononuclear cells (MNC) from whole blood. As shown in FIG. 2, a disposable processing set or fluid circuit 200 (which includes container 14) is mounted on the front panel of centrifuge 10. The processing set (fluid circuit 200) includes a plurality of processing cassettes 23L, 23M and 23R with tubing loops for association with peristaltic pumps on device 10. Fluid circuit 200 also includes a network of tubing and pre-connected containers for establishing flow communication with the patient and for processing and collecting fluids and blood and blood components, as shown in greater detail in FIG. 4. As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

In accordance with the methods and systems described herein, container 68 may also serve as the illumination container, and preferably, illumination container 68 is pre-attached to, and integral with, the disposable set 200. Alternatively, container 68 may be attached to set 200 by known sterile connection techniques, such as sterile docking or the like. In FIG. 2, container 68 is shown as suspended from device 10. However, container 68 may be housed within an adjacent separately housed irradiation device 20 (as shown by broken lines in FIG. 4), thereby eliminating the step of having the operator place container 68 into irradiation device 20.

With reference to FIG. 4, fluid circuit includes inlet line 72, an anticoagulant (AC) line 74 for delivering AC from container 60, an RBC line 76 for conveying red blood cells from chamber 12 of container 14 to container 67, a platelet-poor plasma (PPP) line 78 for conveying PPP to container 66 and line 80 for conveying mononuclear cells to and from separation chamber 14 and collection/illumination container 68. The blood processing set includes one or more venipuncture needle(s) for accessing the circulatory system of the patient. As shown in FIG. 4, fluid circuit 200 includes inlet needle 70 and return needle 82. In an alternative embodiment, a single needle can serve as both the inlet and outlet needle.

Fluid flow through fluid circuit 200 is preferably driven, controlled and adjusted by a microprocessor-based controller in cooperation with the valves, pumps, weight scales and sensors of device 10 and fluid circuit 200, the details of which are described in the previously mentioned U.S. Pat. No. 6,027,657.

In accordance with the present disclosure, the fluid circuit is further adapted for association with the treatment component (i.e., irradiation device) 20. Apparatus for the irradiation of the mononuclear cells are also known and are available from sources such as Cerus Corporation, of Concord, California One example of a suitable irradiation device is described in U.S. Pat. No. 7,433,030, the contents of which is likewise incorporated by reference herein in its entirety. As shown and described in U.S. Pat. No. 7,433,030, irradiation device preferably includes a tray or other holder for receiving one or more containers during treatment. Other irradiation devices may also be suitable for use with the method and system described herein, including devices available from Macopharma and/or Vilber Lourmet.

As noted above, separation chamber 12 is defined by the walls of a flexible processing container 14 carried within an annular gap defined by a rotating spool element 18 and an outer bowl element (not shown). The processing container 14 takes the form of an elongated tube which is wrapped about the spool element 18 before use. The bowl and spool element 18 are pivoted on a yoke between an upright position and a suspended position, also not shown.

When upright, the bowl and spool element 18 are presented for access by the user. A mechanism permits the spool 18 and bowl elements to be opened so that the operator can wrap the container 14 about the spool element 18, as FIG. 3 shows. Pins 150 on the spool element 18 engage cutouts on the container 14 to secure the container 14 on the spool element 18. In operation, the centrifuge 10 rotates the suspended bowl and spool element 18 about an axis 28, creating a centrifugal field within the processing chamber of container 14.

The radial boundaries of the centrifugal field are formed by the interior wall of the bowl element and the exterior wall 26 of the spool element 20. The interior bowl wall defines the high-G wall. The exterior spool wall 26 defines the low-G wall. Further details of the mechanism for causing relative movement of the spool 18 and bowl elements as just described are disclosed in U.S. Pat. No. 5,360,542 entitled "Centrifuge With Separable Bowl and Spool Elements Providing Access to the Separation Chamber," which is also incorporated herein by reference.

Figure 5:
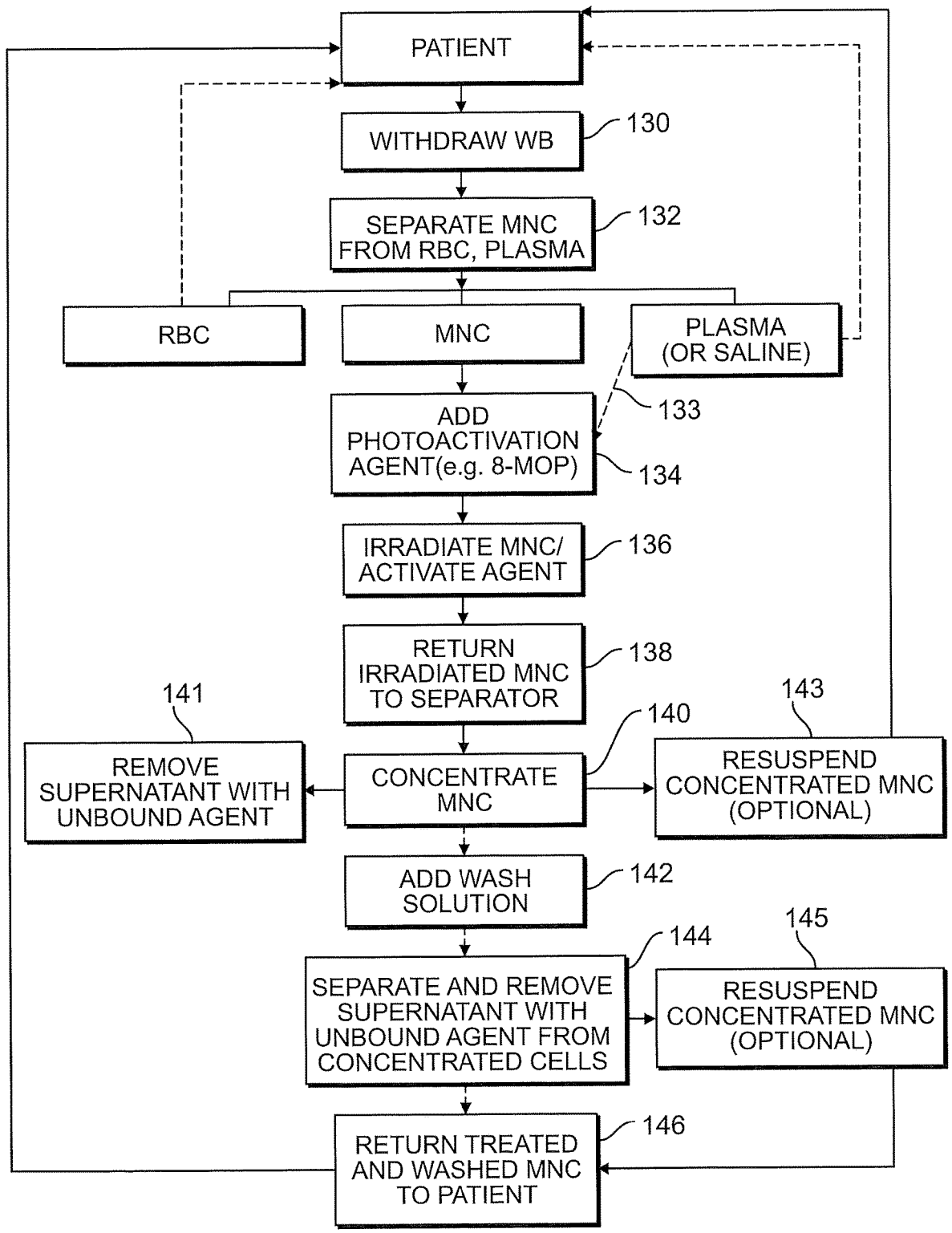
FIG. 5 is a flow chart setting forth the steps of the method of a photopheresis treatment, with washing, as described herein.

An exemplary method of treating mononuclear cells is shown in FIG. 5. The method includes steps in which whole blood is withdrawn from a patient (step 130) through inlet needle 70 and introduced into the separation chamber 12 of container 14 of processing set 200, where the whole blood is subjected to a centrifugal field. The centrifugal field will separate the target cell population, i.e., mononuclear cells, from red blood cells, platelets and plasma (step 132). As discussed above, the components such as red blood cells and platelets may be returned to the patient or may be diverted to a container (e.g., container 67) for further processing.

Collection of the mononuclear cells may proceed in one or more cycles. The number of processing cycles conducted in a given therapeutic procedure will depend upon the total volume of MNC to be collected. For example, in a representative procedure, five collection cycles may be performed sequentially. During each cycle about 1500-3000 ml of whole blood can be processed to obtain a MNC volume of about 3 ml per cycle and a total volume of 15 ml of MNC. As shown in step 132 of FIG. 5, the final volume of mononuclear cells is then provided for further treatment in accordance with the present disclosure. Of course, the collection of MNC is not limited to the method described above. MNCs may be collected in any manner known to those of skill in the art, but preferably using a multifunctional apheresis device.

Effective treatment of the mononuclear cells with light may require that the amount of collected mononuclear cells have a suitable hematocrit. Thus, it may be desired or even necessary to dilute the mononuclear cells with a diluting solution such as plasma or saline, as shown in step 133. In the example described above, approximately 15 ml of MNC may be diluted in about 200 ml of plasma.

The diluted mononuclear cells (in container 68) are then combined with the suitable photoactivation agent in step 134. Alternatively, the desired volume of the agent may be pre-added to the container. As discussed above, for ECP treatment, the compound 8-methoxypsoralen (8-MOP) has been shown to be an effective photoactivation agent. However, other suitable photoactivation agents may be used, including, for example, a psoralen compound. In one example, the system, under the direction of the microprocessor-based controller, may be programmed to automatically deliver the desired amount of photoactive agent from, for example, container 69 before or after the MNC collection, based on the volume of MNC collected or to be collected. For example, 8-MOP may be pre-added to container 68 at the beginning of a particular procedure or alternatively, added to the MNCs collected in the container just prior to irradiation. The 8-MOP is combined with the collected and diluted mononuclear cells to arrive at a mixture having a final 8-MOP concentration of 200 nanograms/mL and/or any effective amount. Typically, the mononuclear cells may be combined with the photoactivation agent to arrive at a final 8-MOP concentration in a range of about 100 to 300 nanograms/mL. The 8-MOP or other photoactivation agent may be added directly to container 68 by a syringe through a port in the container, or added elsewhere in fluid circuit 200 also by a syringe.

Mononuclear cells collected in accordance with the mononuclear cell collection process described above may be collected in container 68 that is suitable for irradiation by light of a selected wavelength. By "suitable" it is meant that the walls of the container are sufficiently transparent to light of the selected wavelength to activate the photoactive agent.

In treatments using UVA light, for example, container walls made of ethylene vinyl acetate (EVA) are suitable. Accordingly, container 68 in which the mononuclear cells are collected may serve both as the collection container and the irradiation container. Container 68 may be placed inside irradiation device 20 by the operator or more preferably, may be placed inside the irradiation chamber of irradiation device 20 at the beginning of the ECP procedure and prior to whole blood withdrawal (as shown by the broken lines representing device 20 in FIG. 4). In any event, container 68 preferably remains integrally connected to the remainder of fluid circuit 200 during the entire procedure, thereby maintaining the closed or functionally closed condition of fluid circuit 200.

As noted above, the fluid circuit 200 is adapted for association with the separation device 10 and with the treatment component (i.e., irradiation device) 20. It will be appreciated that the irradiation device does not have to be integral or even associated with the separation device 10. In fact, the irradiation device 20 is preferably an "adjunct" or independently housed irradiation device 20 used to perform the photopheresis therapy and located adjacent to or in a spaced-apart location from device 10. However, the disposable set 200 (including irradiation container 68) remains connected to the patient during the entire ECP treatment procedure and provides a sterile closed pathway between separation device 10 and the irradiation device 20.

Automated control of the MNC collection and the irradiation treatment may be effected by the microprocessor-based controller of the respective separation device 10 and irradiation device 20 with some operator input for each device. Alternatively, operation of both separation device 10 and irradiation device 20 and the process steps carried out by each may be remotely controlled by a separate controller (e.g., a computer) that communicates with both.

The mononuclear cells with photoactivation agent (8-MOP) are then irradiated for a selected period of time (step 136). In one non-limiting example, during treatment, the mononuclear cell product may be exposed to UV bulbs having a wavelength in the UVA range of about 320 nm to 400 nm for a selected period of time, such as approximately 10-60 minutes, resulting in an average UVA exposure of approximately 0.5-5.0 $J/cm^2$, and preferably approximately 1-2 $J/cm^2$ or even more preferably approximately 1.5 $J/cm^2$ per lymphocyte.

Once treatment is complete, the treated mononuclear cells may be returned to separator 10 (and more specifically, the separation chamber 12 of container 14) as shown in step 138 of FIG. 5. For example, one of the pumps associated with cassette 23R may be actuated (automatically by the controller or under the manual control of the operator) to withdraw the treated MNC from container 68 and introduce the MNC into chamber 12 of container 14. Once inside chamber 12, the MNC may be concentrated (step 140). Supernatant, which will include unbound photoactivation agent is separated from the concentrated and treated cells and diverted to a waste container (step 141).

Concentrating treated MNCs prior to reinfusion allows for the concentrated cells to have a smaller total volume as compared to un-concentrated cells, and as a result, a smaller volume of concentrated MNCs may be reinfused to a patient faster. The concentrated cells may be resuspended in a suitable resuspension medium (e.g., plasma, saline) as shown in step 143 and returned to the patient. Optionally, prior to return to the patient, the concentrated and treated cells may be combined with a suitable wash solution (step 142), supplied (by the pumping action of pumps associated with cassette 23R) from containers 66 and/or 64 (see FIG. 4) is added to the concentrated cells.

Where the concentrated cells are optionally combined with wash solution (as per step 142), the mononuclear cells with wash solution within the chamber 12 (of container 14 of the disposable processing set 200) are subjected to a centrifugal field. The MNC are separated from remaining supernatant (step 144) under the field of centrifugal force. Any remaining unbound and excess photoactive agent will be separated from the concentrated mononuclear cells and suspended in the supernatant. The supernatant may then be withdrawn to a waste container 62 (FIG. 4) while the concentrated and washed mononuclear cells may be resuspended with a resuspension solution (such as, but not limited to, plasma or saline) as shown in step 145, and returned back to the patient, as shown in step 146 of FIG. 5. It will be appreciated that the step of washing the mononuclear cells may be repeated, as necessary. Solutions suitable for washing mononuclear cells include saline, plasma, or any other solution that is compatible with the mononuclear cell apheresis.

In keeping with the disclosure, a method and a system are provided that permit the operator to program the system controller, and to permit the system controller to operate the system, to prioritize the needs of a specific patient. For example, in low weight patients that cannot tolerate extra crystalloid volume due to fluid balance limitations, the operator/controller could operate the system to process less whole blood (thereby using less anticoagulant), and/or increase the % plasma in the suspension of target cells in order to decrease the fluid balance at the end of the procedure. The operator/system could also control the procedure/photoactivation time by varying these same parameters. Thus, prior to step 130, in which whole blood is withdrawn from the patient, the patient and procedure parameters are utilized to control the procedure to, e.g., maintain a patient fluid balance for the procedure within specific limits, have the procedure performed within a time limit specific to the patient, and/or consider plasma clarity when determining a photoactivation time for the suspension of target cells. The patient and procedure parameters may include, but are not limited to, gender, height, weight, hematocrit, fluid balance limit, and procedure time limit. In addition, system parameters may also be considered, such as data reflecting the average intensity of the irradiation source used for photoactivation or the bulb life of the irradiation source.

Figure 6:
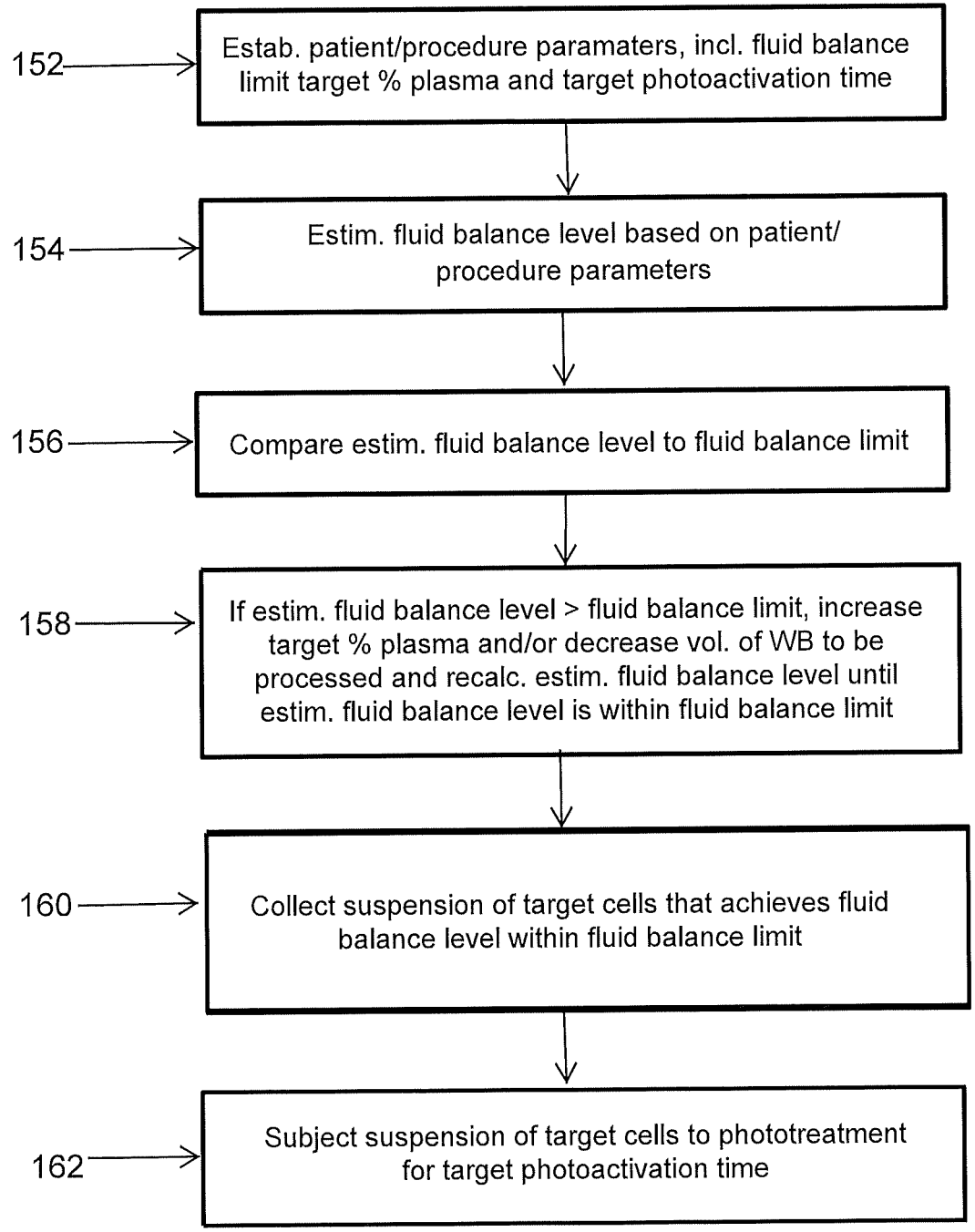
FIG. 6 is a flow chart setting forth the steps of the method of a photopheresis treatment in which the patient's fluid balance is prioritized.

With reference to FIG. 6, if the patient-specific fluid balance level is to be maintained, then, prior to withdrawing whole blood from the patient, patient and procedure parameters, including a patient-specific fluid balance limit, are established (step 152). These parameters may be entered into the controller by the operator or provided by a donor management system. These parameters also include a target % of plasma in the suspension of target cells and a target photoactivation time.

Then, a fluid balance level is estimated based on patient and procedure parameters (step 154), and the estimated fluid balance level is compared to the estimated fluid balance limit (step 156).

If it is determined that the estimated fluid balance level exceeds the estimated fluid balance limit, the target % of plasma in suspension of target cells is increased and the estimated fluid balance recalculated until the recalculated fluid balance is within limit and the target photoactivation time is extended proportionally to target % plasma in suspension of target cells. Additionally, or alternatively, the volume of whole blood to be processed may be decreased and the fluid balance recalculated until the recalculated fluid balance is within the limit (step 158). As noted above; the collection of the target cells may occur in multiple cycles. As such, if the volume of whole blood to be processed is decreased, it may be decreased evenly across multiple cycles, or it may be decreased in a single one of the multiple cycles.

Then the volume of a suspension of target cells that achieves a fluid balance within the estimated fluid balance limit is collected (step 160), and the suspension of target cells to is subjected to phototreatment for the target photoactivation time (step 162). Preferably, the controller is programmed to automatically operate the system to perform each of steps 154-162.

Figure 7:
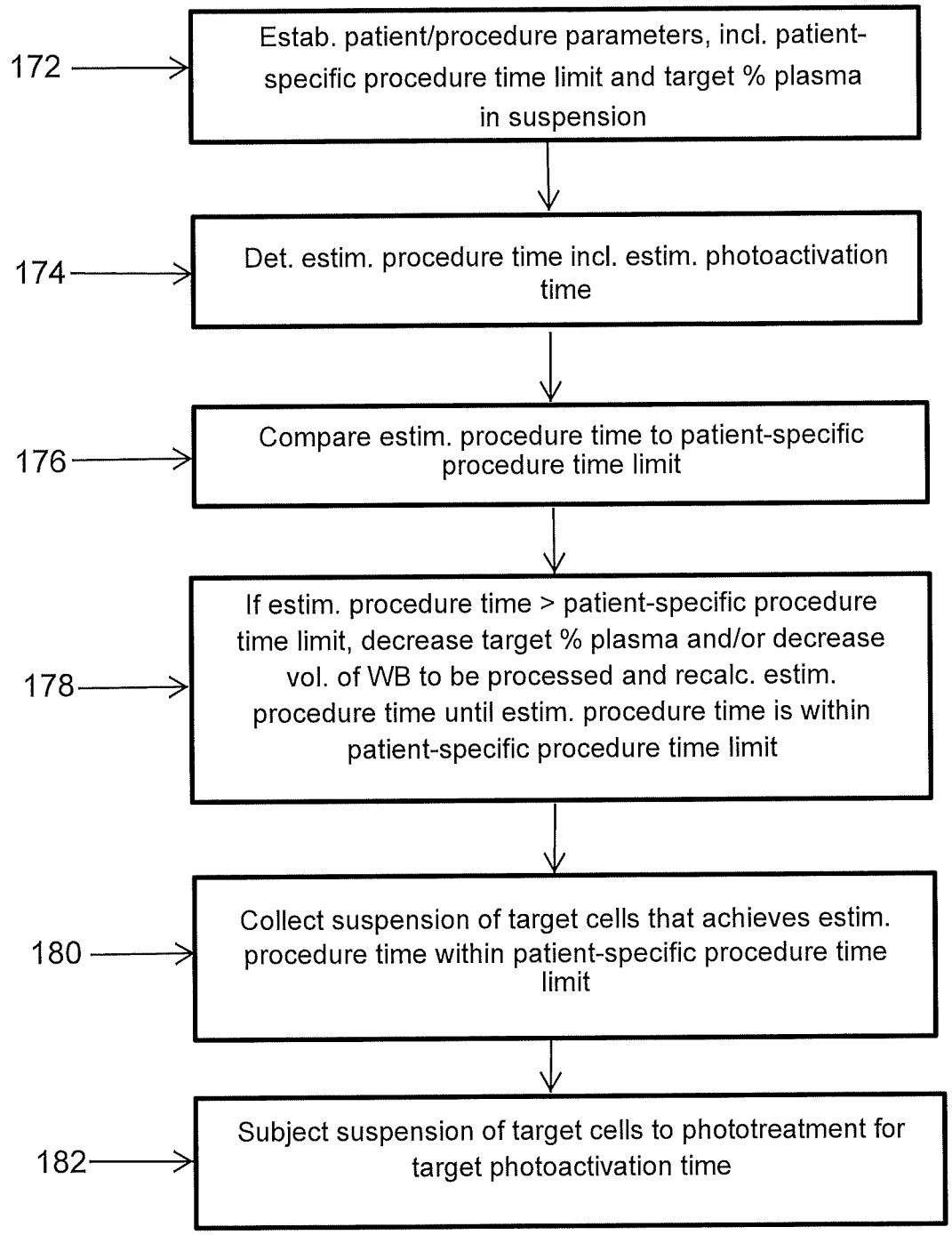
FIG. 7 is a flow chart setting forth the steps of the method of a photopheresis treatment in which the patient's time limit for the procedure is prioritized.

With reference to FIG. 7, if the patient has a time limit within which the procedure is to be performed, then, prior to withdrawing whole blood from the patient, patient and procedure parameters, including the patient-specific procedure time limit, are established. These parameters may be entered into the controller by the operator or provided by a donor management system (step 172).

Then, an estimated procedure time including a photoactivation time is determined based on the patient and procedure parameters, including the target % of plasma in the suspension of target cells (step 174), and the estimated procedure time is compared to the patient-specific procedure time limit (step 176). If the patient-specific procedure time limit is exceeded, then, the target % of plasma in the suspension of target cells is decreased and the estimated target procedure time recalculated until the recalculated target procedure time is within the donor-specific procedure time limit. Alternatively, or additionally, the volume of whole blood to be processed is decreased and the estimated target procedure time recalculated until the recalculated estimated target procedure time is within the patient-specific procedure time limit (step 178). Again, if the volume of whole blood to be processed is decreased, it may be decreased evenly across multiple collection cycles, or it may be decreased in a single one of the multiple cycles.

Then, a suspension of target cells that achieves an estimated procedure time within the donor-specific procedure time limit is collected (step 180); and the suspension of target cells is subjected to phototreatment for the estimated photoactivation time (step 182). Preferably, the controller is programmed to automatically operate the system to perform each of steps 174-182.

Figure 8:
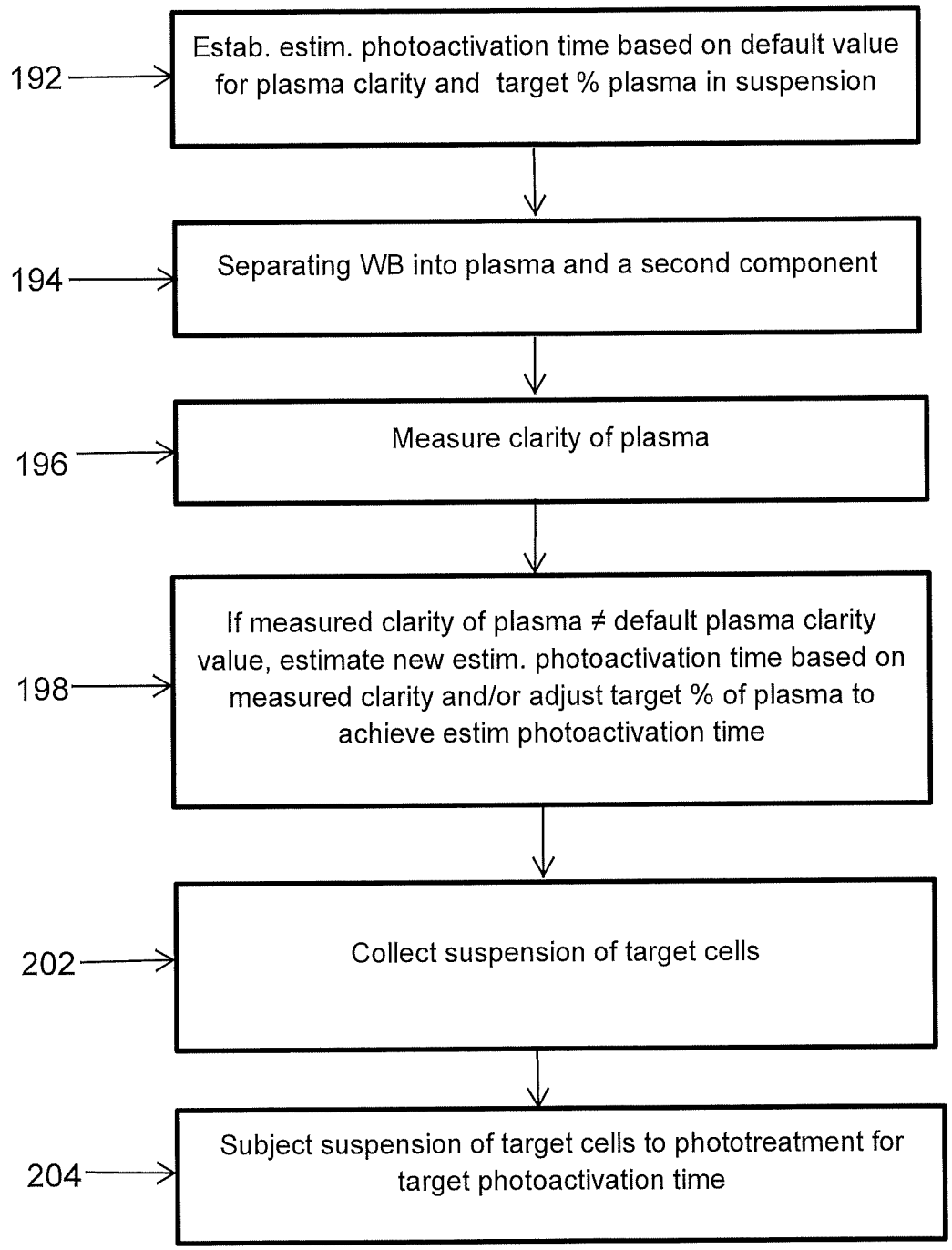
FIG. 8 is a flow chart setting forth the steps of the method of a photopheresis treatment in which the clarity of the patient's plasma is prioritized.

With reference to FIG. 8, if the clarity of the patient's plasma is to be taken into account in determining procedure times, then, prior to withdrawing blood from the patient, patient and procedure parameters are established, including an estimated photoactivation time for the suspension of target cells to be treated based on a default value for plasma clarity and a target % of plasma in suspension of target cells (step 192).

Then, a quantity of whole blood is withdrawn from the donor and separated into a first component comprising plasma and a second component (step 194), and the clarity for the plasma comprising the first component is measured (step 196). The measured clarity value is then compared to the default value for plasma clarity and, if the measured plasma clarity differs from the default value for plasma clarity, a new photoactivation time is estimated based on the measured value for plasma clarity. Alternatively, or additionally, the target % of plasma in suspension of target cells to be treated is adjusted to achieve the estimated photoactivation time (step 198).

A suspension of target cells is then collected (step 202) and subjected to phototreatment for the target photoactivation time (step 204). Preferably, the controller is programmed to automatically operate the system to perform each of steps 192-204.

Figure 9:
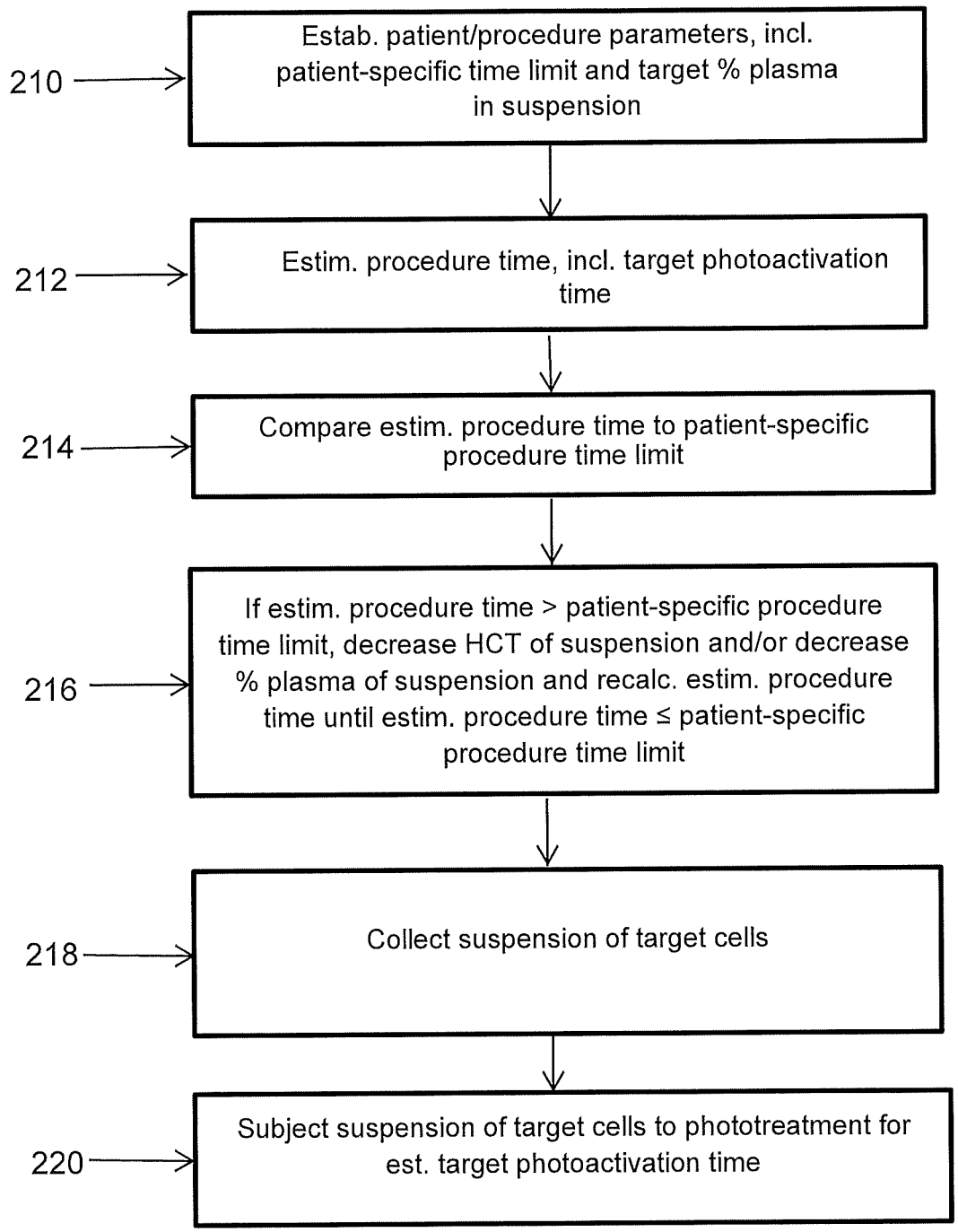
FIG. 9 is a flow chart setting forth the steps of the method of a photopheresis treatment in which the predicted hematocrit of the suspension of target cells and a target % of plasma in the suspension is prioritized.

With reference to FIG. 9, the procedure time is prioritized based on a predicted hematocrit of the suspension of target cells and a target % of plasma in suspension of target cells. First, prior to withdrawing blood from the patient, patient and procedure parameters are established, including a patient-specific procedure time limit and the target % of plasma in suspension of target cells (step 210). Then, an estimated procedure time is determined based on patient and procedure parameters, as well as the target photoactivation time for the suspension of target cells to be treated based on a predicted hematocrit of the suspension of target cells and a target % of plasma in suspension of target cells (step 212).

Then, the estimated target procedure time is compared to the patient-specific procedure time limit (step 214). If the patient-specific procedure time limit is exceeded, the hematocrit of the suspension of target cells is decreased and/or the % of plasma in the suspension of target cells is decreased, and the estimated procedure time (as well as the target photoactivation time) recalculated until the recalculated estimated target procedure time is within the patient-specific procedure time limit (step 216). The hematocrit of the suspension of target cells may be decreased in a number of different ways, including reducing the red blood cell offset in the separator during the collection of the target cells, decreasing the number of collection cycles, adding a crystalloid diluent to the suspension of target cells, and any combination of the foregoing.

Then, the suspension of target cells is collected (step 216), and the suspension of target cells is subjected to phototreatment for the (recalculated) target photoactivation time (step 220). Preferably, the controller is programmed to automatically operate the system to perform each of steps 212-218.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description.

The invention claimed is:

1. A method for photoactivating a suspension of target cells separated from a volume of whole blood comprising:
   a) establishing patient and procedure parameters, including a target % of plasma in the suspension of target cells, a fluid balance limit, and a target photoactivation time;
   b) estimating a fluid balance level based on patient and procedure parameters;
   c) comparing the estimated fluid balance level to the fluid balance limit;
   d) if the fluid balance limit is exceeded, i) increasing the target % of plasma in suspension of target cells and recalculating the estimated fluid balance until the recalculated fluid balance is within the fluid balance limit and extending the target photoactivation time proportional to target % plasma in suspension of target cells and/or ii) decreasing the volume of whole blood to be processed and recalculating the estimated fluid balance until the recalculated fluid balance is within the fluid balance limit;
   e) collecting a suspension of target cells that achieves a fluid balance within the fluid balance limit; and
   f) subjecting the suspension of target cells to phototreatment for the target photoactivation time.

2. The method of claim 1 wherein the suspension of target cells is collected in multiple cycles, and the volume of whole blood to be processed is decreased evenly across the multiple cycles.

3. The method of claim 1 wherein the suspension of target cells is collected in multiple cycles, and the volume of whole blood to be processed is decreased in a single one of the multiple cycles.

4. A method for photoactivating a suspension of target cells separated from a volume of whole blood comprising:
   a) establishing patient and procedure parameters, including a target % of plasma in the suspension of target cells and a patient-specific procedure time limit;
   b) estimating a procedure time including an estimated photoactivation time based on patient and procedure parameters;
   c) comparing the estimated procedure time to the patient-specific procedure time limit;
   d) if the patient-specific procedure time limit is exceeded,
      i) decreasing the target % of plasma in the suspension of target cells and recalculating the estimated procedure time until the recalculated target procedure time is within the patient-specific procedure time limit and/or
      ii) decreasing the volume of whole blood to be processed and recalculating the estimated procedure time until the recalculated estimated procedure time is within the patient-specific procedure time limit;
   e) collecting a suspension of target cells that achieves an estimated procedure time within the patient-specific procedure time limit; and
   f) subjecting the suspension of target cells to phototreatment for the estimated photoactivation time.

5. The method of claim 4 wherein the suspension of target cells is collected in multiple cycles, and the volume of whole blood to be processed is decreased evenly across the multiple cycles.

6. The method of claim 4 wherein the suspension of target cells is collected in multiple cycles, and the volume of whole blood to be processed is decreased in a single one of the multiple cycles.

7. A method for photoactivating a suspension of target cells separated from a volume of whole blood comprising:
   a) establishing patient and procedure parameters, including an estimated photoactivation time for the suspension of target cells to be treated based on a default value for plasma clarity and a target % of plasma in suspension of target cells;
   b) separating whole blood into a first component comprising plasma and a second component;
   c) measuring a clarity for the plasma comprising the first component;
   d) comparing the measured plasma clarity to the default value for plasma clarity;
   e) if the measured plasma clarity differs from the default value for plasma clarity, estimating a new photoactivation time based on the measured value for plasma clarity and/or adjusting the target % of plasma in suspension of target cells to be treated to achieve the estimated photoactivation time;
   f) collecting the suspension of target cells; and
   g) subjecting the suspension of target cells to phototreatment for the estimated photoactivation time.

8. A method for photoactivating a suspension of target cells separated from a volume of whole blood comprising:
  a) establishing patient and procedure parameters, including a target % of plasma in the suspension of target cells and a patient-specific procedure time limit;
  b) estimating a procedure time including a target photoactivation time based on patient and procedure parameters;
  c) comparing the estimated procedure time to the patient-specific procedure time limit;
  d) if the patient-specific procedure time limit is exceeded,
    i) decreasing a hematocrit of the suspension of target cells and/or decreasing the % of plasma in the suspension of target cells, and recalculating the estimated procedure time until the recalculated estimated procedure time is within patient-specific procedure time limit;
  e) collecting the suspension of target cells; and
  f) subjecting the suspension of target cells to phototreatment for the estimated target photoactivation time.

9. The method of claim 8 wherein the hematocrit of the suspension of target cells is decreased by reducing an offset of red blood cells during the collection of the target cells.

10. The method of claim 8 wherein the suspension of target cells is collected in a number of multiple cycles, and the hematocrit of the suspension of target cells is decreased by decreasing the number of cycles.

11. The method of claim 8 wherein the hematocrit of the suspension of target cells is decreased by adding a crystalloid diluent to the suspension of target cells.

12. An online extracorporeal photopheresis system for photoactivating a suspension of target cells separated from a volume of whole blood comprising:
  (a) a disposable fluid circuit comprising:
    i. a processing chamber for separating whole blood into one or more components including mononuclear cells,
    ii. at least one storage container adapted to receive mononuclear cells wherein at least a portion of said container is transparent to light of a selected wavelength;
  (b) a separation device adapted to receive said processing chamber for effecting separation of said mononuclear cells from whole blood;
  (c) an irradiation device housed separately from said separation device adapted to receive said mononuclear cell storage container for treating said mononuclear cells with a selected dose of light; and
  (d) a programmable controller programmed to automatically perform the steps of a method for photoactivating a suspension of target cells separated from a volume of whole blood, wherein the programmable controller is configured to automatically perform the steps of:
    estimating a fluid balance level based on patient and procedure parameters;
    comparing the estimated fluid balance level to a fluid balance limit;
    if the fluid balance limit is exceeded, i) increasing the target % of plasma in suspension of target cells and recalculating the estimated fluid balance until the recalculated fluid balance is within limit and extending a target photoactivation time proportional to target % plasma in suspension of target cells and/or ii) decreasing the volume of whole blood to be processed and recalculating the estimated fluid balance until the recalculated fluid balance is within fluid balance limit;
    collecting a suspension of target cells that achieves a fluid balance within the fluid balance limit; and
    subjecting the suspension of target cells to phototreatment for the target photoactivation time.

13. An online extracorporeal photopheresis system for photoactivating a suspension of target cells separated from a volume of whole blood comprising:
  (a) a disposable fluid circuit comprising:
    i. a processing chamber for separating whole blood into one or more components including mononuclear cells,
    ii. at least one storage container adapted to receive mononuclear cells wherein at least a portion of said container is transparent to light of a selected wavelength;
  (b) a separation device adapted to receive said processing chamber for effecting separation of said mononuclear cells from whole blood;
  (c) an irradiation device housed separately from said separation device adapted to receive said mononuclear cell storage container for treating said mononuclear cells with a selected dose of light; and
  (d) a programmable controller programmed to automatically perform the steps of a method for photoactivating a suspension of target cells separated from a volume of whole blood, wherein the programmable controller is configured to automatically perform the steps of:
    estimating a procedure time including an estimated photoactivation time based on patient and procedure parameters;
    comparing the estimated procedure time to a patient-specific procedure time limit;
    if the patient-specific procedure time limit is exceeded, i) decreasing the target % of plasma in the suspension of target cells and recalculating the estimated procedure time until the recalculated target procedure time is within the patient-specific procedure time limit and/or ii) decreasing the volume of whole blood to be processed and recalculating the estimated procedure time until the recalculated estimated procedure time is within the patient-specific procedure time limit;
    collecting a suspension of target cells that achieves an estimated procedure time within the patient-specific procedure time limit; and
    subjecting the suspension of target cells to phototreatment for the estimated photoactivation time.

14. An online extracorporeal photopheresis system for photoactivating a suspension of target cells separated from a volume of whole blood comprising:
  (a) a disposable fluid circuit comprising:
    i. a processing chamber for separating whole blood into one or more components including mononuclear cells,
    ii. at least one storage container adapted to receive mononuclear cells wherein at least a portion of said container is transparent to light of a selected wavelength;
  (b) a separation device adapted to receive said processing chamber for effecting separation of said mononuclear cells from whole blood;
  (c) an irradiation device housed separately from said separation device adapted to receive said mononuclear cell storage container for treating said mononuclear cells with a selected dose of light, and;
  (d) a programmable controller programmed to automatically perform the steps of a method for photoactivating a suspension of target cells separated from a volume of whole blood, wherein the programmable controller is configured to automatically perform the steps of:

establishing patient and procedure parameters, including an estimated photoactivation time for the suspension of target cells to be treated based on a default value for plasma clarity and a target % of plasma in suspension of target cells;

separating whole blood into a first component comprising plasma and a second component;

measuring a clarity for the plasma comprising the first component;

comparing the measured plasma clarity to the default value for plasma clarity;

if the measured plasma clarity differs from the default value for plasma clarity, estimating a new photoactivation time based on the measured value for plasma clarity and/or adjusting the target % of plasma in suspension of target cells to be treated to achieve the estimated photoactivation time;

collecting the suspension of target cells; and subjecting the suspension of target cells to phototreatment for the estimated photoactivation time.

15. An online extracorporeal photopheresis system for photoactivating a suspension of target cells separated from a volume of whole blood comprising:

(a) a disposable fluid circuit comprising:
  i. a processing chamber for separating whole blood into one or more components including mononuclear cells,
  ii. at least one storage container adapted to receive mononuclear cells wherein at least a portion of said container is transparent to light of a selected wavelength;

(b) a separation device adapted to receive said processing chamber for effecting separation of said mononuclear cells from whole blood;

(c) an irradiation device housed separately from said separation device adapted to receive said mononuclear cell storage container for treating said mononuclear cells with a selected dose of light; and (d) a programmable controller programmed to automatically perform the steps of a method for photoactivating a suspension of target cells separated from a volume of whole blood, wherein the programmable controller is configured to automatically perform the steps of:

i. estimating a procedure time including a target photoactivation time based on patient and procedure parameters;

comparing the estimated procedure time to a patient-specific procedure time limit;

if the patient-specific procedure time limit is exceeded, i) decreasing a hematocrit of the suspension of target cells and/or decreasing the % of plasma in the suspension of target cells, and recalculating the estimated procedure time until the recalculated estimated procedure time is within patient-specific procedure time limit;

collecting the suspension of target cells; and subjecting the suspension of target cells to phototreatment for the estimated target photoactivation time; and ii. estimating a fluid balance level based on patient and procedure parameters;

comparing the estimated fluid balance level to a fluid balance limit;

if the fluid balance limit is exceeded, i) increasing the target % of plasma in suspension of target cells and recalculating the estimated fluid balance until the recalculated fluid balance is within limit and extending a target photoactivation time proportional to target % plasma in suspension of target cells and/or ii) decreasing the volume of whole blood to be processed and recalculating the estimated fluid balance until the recalculated fluid balance is within fluid balance limit;

collecting a suspension of target cells that achieves a fluid balance within the fluid balance limit; and subjecting the suspension of target cells to phototreatment for the target photoactivation time.

16. An online extracorporeal photopheresis system for photoactivating a suspension of target cells separated from a volume of whole blood comprising:

(a) a disposable fluid circuit comprising:
  i. a processing chamber for separating whole blood into one or more components including mononuclear cells,
  ii. at least one storage container adapted to receive mononuclear cells wherein at least a portion of said container is transparent to light of a selected wavelength;

(b) a separation device adapted to receive said processing chamber for effecting separation of said mononuclear cells from whole blood;

(c) an irradiation device housed separately from said separation device adapted to receive said mononuclear cell storage container for treating said mononuclear cells with a selected dose of light; and (d) a programmable controller programmed to automatically perform the steps of a method for photoactivating a suspension of target cells separated from a volume of whole blood, wherein the programmable controller is configured to automatically perform the steps of:

estimating a procedure time including a target photoactivation time based on patient and procedure parameters;

comparing the estimated procedure time to a patient-specific procedure time limit;

if the patient-specific procedure time limit is exceeded, i) decreasing a hematocrit of the suspension of target cells and/or decreasing the % of plasma in the suspension of target cells, and recalculating the estimated procedure time until the recalculated estimated procedure time is within patient-specific procedure time limit;

collecting the suspension of target cells; and subjecting the suspension of target cells to phototreatment for the estimated target photoactivation time.

* * * * *